United States Patent
Murata et al.

(10) Patent No.: US 8,534,835 B2
(45) Date of Patent: Sep. 17, 2013

(54) OPTICAL TOMOGRAPHIC IMAGE PHOTOGRAPHING APPARATUS

(75) Inventors: Toshio Murata, Aichi (JP); Yukihiro Higuchi, Aichi (JP)

(73) Assignee: Nidek Co., Ltd., Aichi (JP)

( * ) Notice: Subject to any disclaimer, the term of this patent is extended or adjusted under 35 U.S.C. 154(b) by 197 days.

(21) Appl. No.: 13/034,147

(22) Filed: Feb. 24, 2011

(65) Prior Publication Data

US 2011/0205490 A1 Aug. 25, 2011

(30) Foreign Application Priority Data

Feb. 25, 2010 (JP) ................... 2010-040586

(51) Int. Cl.
*A61B 3/14* (2006.01)

(52) U.S. Cl.
USPC .......................................................... 351/206

(58) Field of Classification Search
USPC .......................................................... 351/206
See application file for complete search history.

(56) References Cited

U.S. PATENT DOCUMENTS

| | | | |
|---|---|---|---|
| 7,306,336 B2 | 12/2007 | Akita et al. | |
| 7,643,154 B2 | 1/2010 | Kikawa et al. | |
| 2008/0100612 A1 | 5/2008 | Datmalchi et al. | |
| 2010/0014089 A1 | 1/2010 | Yamada et al. | |

FOREIGN PATENT DOCUMENTS

| | | |
|---|---|---|
| EP | 1775545 A2 | 4/2007 |
| EP | 2130486 A1 | 12/2009 |
| JP | 2005185590 | 7/2005 |
| JP | 2008154939 | 7/2008 |
| JP | 2010012111 | 1/2010 |

OTHER PUBLICATIONS

Pircher et al., "Simultaneous SLO/OCT imaging of the human retina with axial eye motion correction," Optics Express Dec. 12, 2007, Optical Society of America, US, vol. 15, No. 25, Dec. 12, 2007, pp. 16922-16932.
Extended European Search Report for European Patent Application No. 11155669.2 dated Jun. 27, 2011.

*Primary Examiner* — Jack Dinh
(74) *Attorney, Agent, or Firm* — Lowe Hauptman & Ham, LLP (57) ABSTRACT

An optical tomographic image photographing apparatus includes: an interference optical system for combining reflected light with reference light on an object to guide the combined light to a detector; a driving part for moving an optical member in an optical-axis direction in order to adjust an optical path difference between measurement light and the reference light; an image obtaining part for obtaining a tomographic image of the object based on a light receiving signal output from the detector; and a control unit configured to detect positional deviation with respect to a depth direction in the tomographic image and to correct a display position of the tomographic image such that the tomographic image is displayed in a predetermined position within a display region on a monitor.

16 Claims, 3 Drawing Sheets

OPTICAL TOMOGRAPHIC IMAGE PHOTOGRAPHING APPARATUS

CROSS-REFERENCE TO RELATED APPLICATION

This application is based on Japanese Patent Application No. 2010-040586 filed with the Japan Patent Office on Feb. 25, 2010, the entire content of which is hereby incorporated by reference.

BACKGROUND

1. Technical Field

An aspect of the invention is related to an optical tomographic image photographing apparatus for photographing a tomographic image of an object.

2. Related Art

There is known an optical tomographic image photographing apparatus (Optical Coherence Tomography: OCT) which has an interference optical system and photographs a tomographic image of an object. The optical interference optical system of this apparatus splits a light flux emitted from a light source into a measurement light flux and a reference light flux. This optical interference optical system then guides the measurement light flux to an object, while guiding the reference light flux to a reference optical system. Subsequently, the optical interference optical system combines the measurement light flux, reflected on the object, with the reference light flux, to obtain interference light, and thereafter makes a light receiving device receive this interference light. This apparatus is used for, for example, obtaining a tomographic image of a living body such as an eyeball or skin.

This kind of apparatus also includes an apparatus which displays a tomographic image at a predetermined position on a display monitor by changing an optical path difference between a measurement light and a reference light at any time, even if the object moves while being photographed (refer to JP-A-2008-154939). In such an apparatus, an optical-path-length varying member (for example, a reference mirror) is moved by driving a motor in order to change the optical path difference.

SUMMARY

However, in the case of a configuration like that described above, if the object moves due to breathing or a slight quiver of the body, the position of the reference mirror will be constantly adjusted. Therefore, the tomographic image would end up being difficult to see. Further, it is possible that blurring may occur in the tomographic image on the monitor due to vibrations of a motor generated when the reference mirror is moved.

A technical object of an aspect of the invention is to provide an optical tomographic image photographing apparatus which enhances the visibility of a tomographic image movie-displayed on a monitor.

The aspect of the invention includes the following configuration.

An optical tomographic image photographing apparatus for photographing a tomographic image of an object, includes: an interference optical system including: a measurement light source; and a splitter that splits light emitted from the measurement light source, such that the light is split in a measurement optical path for guiding part of the light to the object as measurement light and in a reference optical path for generating reference light, the interference optical system combining reflected light from the measurement optical path, the reflected light being obtained by reflection of the measurement light on the object, with the reference light from the reference optical path, to guide combined light to a detector; an optical scanner that is arranged in the measurement optical path for scanning the measurement light on the object; a driving part for moving an optical member arranged in the measurement optical path or the reference optical path in an optical-axis direction in order to adjust an optical path difference between the measurement optical path and the reference optical path; an image obtaining part that is connected to the detector for obtaining a tomographic image of the object based on a light receiving signal output from the detector; a monitor; and a control unit configured to detect positional deviation of the tomographic image in a depth direction thereof based on the signal output from the detector, and to correct a display position of the tomographic image such that the tomographic image obtained by the image obtaining part is displayed in a predetermined position on the monitor by controlling a display of the monitor based on the detected positional deviation.

In accordance with this aspect of the invention, the visibility of a tomographic image movie-displayed on a monitor is enhanced.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Preferred embodiments of the invention will be described below with reference to the accompanying drawings, in which like reference characters designate similar or identical parts throughout the several views thereof.

Figure 1:
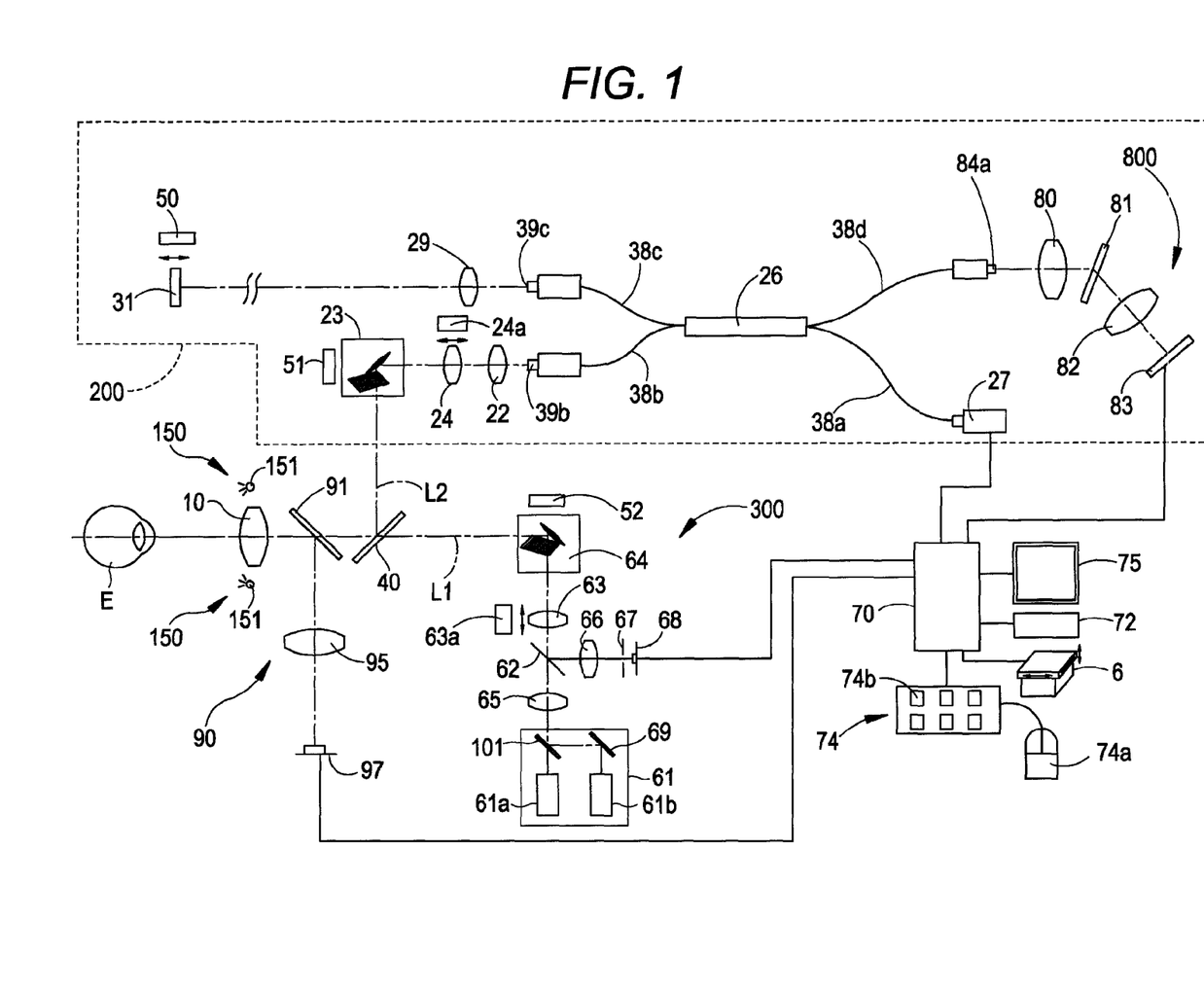
FIG. 1 is a view showing an optical system and a control system of an ophthalmic photographing apparatus of an embodiment of the invention.

An embodiment in accordance with an aspect of the invention will be described based on the drawings. FIG. 1 illustrates an optical system and a control system in an optical tomographic image photographing apparatus of an embodiment of the invention. In the embodiment, a fundus photographing apparatus as an example of an ophthalmic photographing apparatus will be described. It is to be noted that in the embodiment, a description is given with a depth direction of an examinee's eye referred to as a Z-direction (direction of optical axis L1), a horizontal direction referred to as an X-direction, and a vertical direction referred to as a Y-direction.

As shown in FIG. 1, the optical system of this ophthalmic photographing apparatus is broadly divided into an interference optical system (hereinafter referred to as OCT optical system) 200 and a scanning laser ophthalmoscope (SLO) optical system 300. The OCT optical system 200 serves to obtain a tomographic image of a fundus of an examinee's eye E by use of an optical interference technique. Meanwhile, the SLO optical system 300 illuminates the fundus by use of infrared light, to obtain an SLO fundus image for observing the fundus. It is to be noted that each of the above optical systems has a light projecting optical system and a light receiving optical system, and is used as a photographing optical system for obtaining a photographed image of the eye. The light projecting optical system projects at least part of light emitted from a light source to a predetermined region of the eye. The photographing optical system receives reflected light from the predetermined region of the eye in a light receiving device.

As the OCT optical system 200, there has been used an OCT optical system of a spectral domain type. Naturally, a time domain type (TD-OCT) or a swept source domain type (SS-OCT) may also be used. It is to be noted that the OCT optical system 200 and the SLO optical system 300 are incorporated in a housing (not illustrated). Further, this housing is three-dimensionally moved with respect to the eye E by a known (manual or electrically-powered) movement mechanism for alignment.

It is to be noted that a dichroic mirror 40 is used as a light splitting member. The dichroic mirror 40 has a characteristic of reflecting measurement light (e.g., λ=about 840 nm) emitted from a measurement light source 27 provided in the OCT optical system 200, while being transmitted by laser light (light with a different wavelength from that of the light source 27, e.g., λ=about 780 nm) emitted from a light emitting part 61 provided in the SLO optical system 300. The dichroic mirror 40 makes a measurement optical axis L2 of the OCT optical system 200 and a measurement optical axis L1 of the SLO optical system 300 be the same axial.

A configuration of the OCT optical system 200 provided on the reflection side to the dichroic mirror 40 will be described. The OCT optical system 200 splits a light flux emitted from the light source into a measurement light flux and a reference light flux. Further, the OCT optical system 200 guides the measurement light flux to a predetermined region of the eye (anterior segment or fundus), while guiding the reference light flux to the reference optical system. Subsequently, the OCT optical system 200 makes the light receiving device receive interference light obtained by combining the measurement light flux, reflected on the predetermined region of the eye, with the reference light flux.

The OCT light source 27 emits low coherent light. As the OCT light source 27, there is for example used a light source that emits light with a central wavelength of 840 nm and a band width of 50 nm (e.g., SLD light source). A fiber coupler 26 serves as a light splitting member as well as a light coupling member. The light emitted from the OCT light source 27 passes through an optical fiber 38*a* as a guiding optical path, and is thereafter split by the coupler 26 into reference light and measurement light. The measurement light travels toward the eye E via an optical fiber 38*b*, while the reference light travels toward a reference mirror 31 via an optical fiber 38*c*.

In an optical path for emitting the measurement light toward the eye E, an end 39*b* of the optical fiber 38*b*, a collimator lens 22, a focusing lens 24 and a scanning part 23 are arranged. The focusing lens 24 is movable in the optical-axis direction in line with a refraction error of the eye E for adjustment of a focus on the fundus. The scanning part 23 is capable of scanning the fundus in XY directions with the measurement light. This scanning part 23 includes two galvanometer mirrors, and is operated by driving of a scanning driving mechanism 51. The dichroic mirror 40 and an objective lens 10 serve as a light guiding optical system for guiding OCT measurement light from the OCT optical system 200 to the fundus. It is to be noted that the scanning part 23 of the embodiment arbitrarily adjusts a reflection angle of the measurement light by means of the two galvanometer mirrors. Hence a direction of scanning by means of the measurement light on the fundus is arbitrarily set. A tomographic image in an arbitrary area of the fundus is thus obtained. It is to be noted that the end 39*b* of the optical fiber 38*b* is arranged in a position conjugate with the fundus of the eye E. Further, the two galvanometer mirrors of the scanning part 23 are position arranged in a position substantially conjugate with a pupil of the eye E.

The galvanometer mirrors and the scanning driving mechanism 51 described above are used as an optical scanner (optical scanning part). The optical scanner is arranged in the optical path for the measurement light flux (measurement optical path). The optical scanner changes a traveling direction of the measurement light flux in order to scan the predetermined region of the eye in a transverse direction (XY directions) with the measurement light flux. As the optical scanner, other than the mirror, an acousto-optic device (AOM: Acousto-Optic Modulator) for changing a traveling (deflection) direction of light, and the like are used.

The measurement light emitted from the end 39*b* of the optical fiber 38*b* is collimated by the collimator lens 22, and thereafter reaches the scanning part 23 via the focusing lens 24. In this scanning part 23, the two galvanometer mirrors are driven, to change a reflecting direction of the measurement light. The measurement light reflected on the scanning part 23 is reflected on the dichroic mirror 40, and thereafter collected in the fundus via a dichroic mirror 91 and the objective lens 10.

The measurement light reflected on the fundus passes through the objective lens 10 and the dichroic mirror 91, and is thereafter reflected on the dichroic mirror 40, to travel toward the OCT optical system 200. Further, the measurement light is incident on the end 39*b* of the optical fiber 38*b* via the two galvanometer mirrors of the scanning part 23, the focusing lens 24 and the collimator lens 22. The measurement light incident on the end 39*b* reaches an end 84*a* of an optical fiber 38*d* via the optical fiber 38*b*, the fiber coupler 26 and the optical fiber 38*d*.

Meanwhile, in an optical path for emitting reference light toward the reference mirror 31 (reference optical path), an end 39*c* of the optical fiber 38*c*, a collimator lens 29 and the reference mirror 31 are arranged. The reference mirror 31 is configured to be movable in the optical-axis direction by a reference mirror driving mechanism 50. This allows the reference mirror 31 to change an optical path length of the reference light. That is, in this case, the reference mirror 31 is used as an optical-path-length varying member.

The reference light emitted from the end 39*c* of the optical fiber 38*c* is made to be a parallel light flux by the collimator lens 29 and reflected on the reference mirror 31, and is thereafter collected by the collimator lens 29, to be incident on the end 39*c* of the optical fiber 38*c*. The reference light incident on the end 39*c* reaches the coupler 26 via the optical fiber 38*c*.

The reference light generated as described above and the fundus reflected light obtained by reflection of the measurement light on the fundus are combined in the coupler 26, to become interference light. The interference light is emitted from the end 84*a* through the optical fiber 38*d*.

A spectroscopic optical system 800 (spectrometer part) splits the interference light into each frequency component for obtaining an interference signal with reference to each frequency. The spectroscopic optical system 800 has a collimator lens 80, a grating (diffraction grating) 81, a condenser lens 82 and a light receiving device (detector) 83. The light receiving device 83 includes a one-dimensional device (line sensor) having the sensitivity to light with a wavelength in an infrared region.

The light emitted from the end 84a is made to be parallel light in the collimator lens 80, and thereafter split in the grating 81 into each frequency component (each wavelength component). The split light is then collected on the light receiving surface of the light receiving device 83 via the condenser lens 82. Thereby, spectrum information with interference fringes is recorded in the light receiving device 83. The spectrum information (light receiving signal) is then input into a control part 70. The control part 70 analyzes the spectrum information by use of Fourier transformation, to measure information (A-scan signal) in the depth direction of the eye. Using the scanning part 23, the control part 70 scans the fundus in a predetermined transverse direction with the measurement light, to obtain a tomographic image. For example, the control part 70 scans the fundus in the X-direction or the Y-direction with the measurement light, to obtain a tomographic image of the fundus in an X-Z plane or a Y-Z plane (it is to be noted that in the embodiment, such a method for one-dimensionally scanning the fundus with the measurement light to obtain a tomographic image is referred to as B-scan). In addition, the obtained tomographic image is stored in a memory 72 connected to the control part 70. Further, the control part 70 scans two-dimensionally the fundus in the XY directions with the measurement light, to obtain a three-dimensional image of the fundus. Meanwhile, in the embodiment, an OCT image is obtained by the two galvanometer mirrors provided on the scanning part 23

Next, the SLO optical system (confocal optical system) 300 arranged in a transmitting direction of the dichroic mirror 40 will be described. The SLO optical system 300 is broadly divided into an illuminating optical system for illuminating the fundus and a light receiving optical system for receiving, with the light receiving device, reflected light from the fundus illuminated by the illuminating optical system. The SLO optical system 300 obtains a front image of the fundus based on a light receiving signal output from the light receiving device.

The light emitting part 61 has a first light source (SLO light source) 61a, a second light source (fixation optical system) 61b, a mirror 69, and a dichroic mirror 101. The first light source 61a emits light with a wavelength in the infrared region (e.g., λ=780 nm), and the second light source 61b emits light with a wavelength in a visible region (e.g., λ=630 nm). It is to be noted that as the first light source 61a and the second light source 61b, a light source is used which emits light with high luminance and high directivity (such as a laser diode light source or an SLD light source). Infrared light emitted from the first light source 61a passes through the dichroic mirror 101, and travels to a beam splitter 62 through a collimator lens 65. Visible light emitted from the second light source 61b is bent by the mirror 69, and thereafter reflected on the dichroic mirror 101. This visible light then travels along the same axis as that of the infrared light emitted from the first light source 61a. The first light source 61a is used for obtaining a fundus front image for observation. Meanwhile, the second light source 61b is used for guiding the sight direction of the eye.

In the optical path for emitting laser light from the light emitting part 61 toward the eye E, the collimator lens 65, a focusing lens 63, the scanning part (optical scanner) 64 and the objective lens 10 are arranged. The focusing lens 63 is movable in the optical-axis direction in line with a refraction error of the eye. The scanning part 64 performs high-speed scanning on the fundus in the XY directions with the measurement light. The scanning part 64 has a galvanometer mirror and a polygon mirror, and is driven by a scanning driving mechanism 52. Reflected surfaces of the galvanometer mirror and the polygon mirror are arranged in a position substantially conjugate with the pupil of the eye E.

Further, the beam splitter 62 is arranged between the light emitting part 61 and the focusing lens 63. Moreover, on the reflecting direction of the beam splitter 62, a condenser lens 66, a confocal opening 67 and a light receiving device 68 for SLO are provided. The condenser lens 66 serves to configure the confocal optical system. The confocal opening 67 is arranged in a position conjugate with the fundus.

Herein, laser light (measurement light or fixation light) emitted from the light emitting part 61 transmits the beam splitter 62 via the collimator lens 65, and thereafter passes through the focusing lens 63. Subsequently, this laser light reaches the scanning part 64. By driving of the galvanometer mirror and the polygon mirror, the reflecting direction of this laser light is changed. The reflected laser light transmits the dichroic mirror 40, and is thereafter collected in the fundus via the dichroic mirror 91 and the objective lens 10.

The laser light (measurement light) reflected on the fundus passes through the objective lens 10, the dichroic mirror 91, the galvanometer mirror and the polygon mirror of the scanning part 64 and the focusing lens 63, and is then reflected on the beam splitter 62. Subsequently, this laser light is collected in the condenser lens 66, and thereafter detected by the light receiving device 68 via the confocal opening 67. A light receiving signal generated in the light receiving device 68 is input into the control part 70. The control part 70 obtains the front image of the fundus based on the light receiving signal obtained in the light receiving device 68. The obtained front image is stored in the memory 72. It is to be noted that at the time of obtaining the front image (SLO image), scanning (sub-scanning) of laser light in a longitudinal direction by means of the galvanometer mirror provided in the scanning part 64 and scanning (main scanning) of laser light in a transverse direction by means of the polygon mirror are implemented.

<Alignment Target Projecting Optical System>

Further, the ophthalmic photographing apparatus of the embodiment has a projecting optical system 150 for projecting an alignment target to an examinee's eye. This projecting optical system 150 has an infrared light source 151, and is also arranged outside an inspection window (observation window) provided in the apparatus housing. Further, this projecting optical system 150 projects the target diagonally from the front of the eye E (the outside of the objective lens 10 in the radial direction).

<Anterior-Segment Observing Optical System>

An observing optical system 90 is provided with the objective lens 10, the dichroic mirror 91, an image forming lens 95, and a two-dimensional photographing device (two-dimensional light receiving device) 97. This observing optical system 90 is arranged for photographing the eye E, to obtain the anterior-segment image. The dichroic mirror 91 has a characteristic of reflecting light with a wavelength emitted from the infrared light source 151, while being transmitted by the other light.

The reflected light (including alignment light) obtained by reflection of the light, emitted from the infrared light source 151, on the anterior segment passes through the objective lens 10 and is reflected by the dichroic mirror 91. Thereafter, the light is received by the two-dimensional photographing device 97 via the image forming lens 95. Thereby, the two-dimensional photographing device 97 photographs the anterior-segment image. This anterior-segment image photographed by the photographing device 97 is output to the control part 70, while being displayed on the monitor 75.

It is to be noted that the control part 70 is connected to the display monitor 75, and controls a display image thereof. Further, the control part 70 is connected with a memory (storing part) 72, an operating part 74 for performing a variety of operations, the scanning driving mechanism 51, the scanning driving mechanism 52, the reference mirror driving mechanism 50, a first driving mechanism 63a for moving the focusing lens 63 in the optical-axis direction, a second driving mechanism 24a for moving the focusing lens 24 in the optical-axis direction, and the like. It is to be noted that as the monitor 75, two monitors, i.e., a monitor for alignment observation and a monitor for photographed image observation, may be used or one shared monitor may naturally be used.

Next, the overall operation of the apparatus will be described. The control part 70 forms a tomographic image of the fundus based on an output signal from the light receiving element 83. Further, the control part 70 forms a front image of the fundus based on an output signal from the light receiving element 68 (refer to FIG. 2). The control part 70 then moves the reference mirror 31 by controlling the driving of the driving mechanism 50. The control part 70 further controls the monitor 75 to display the obtained tomographic image within a predetermined display region (refer to FIG. 2).

Figure 3:
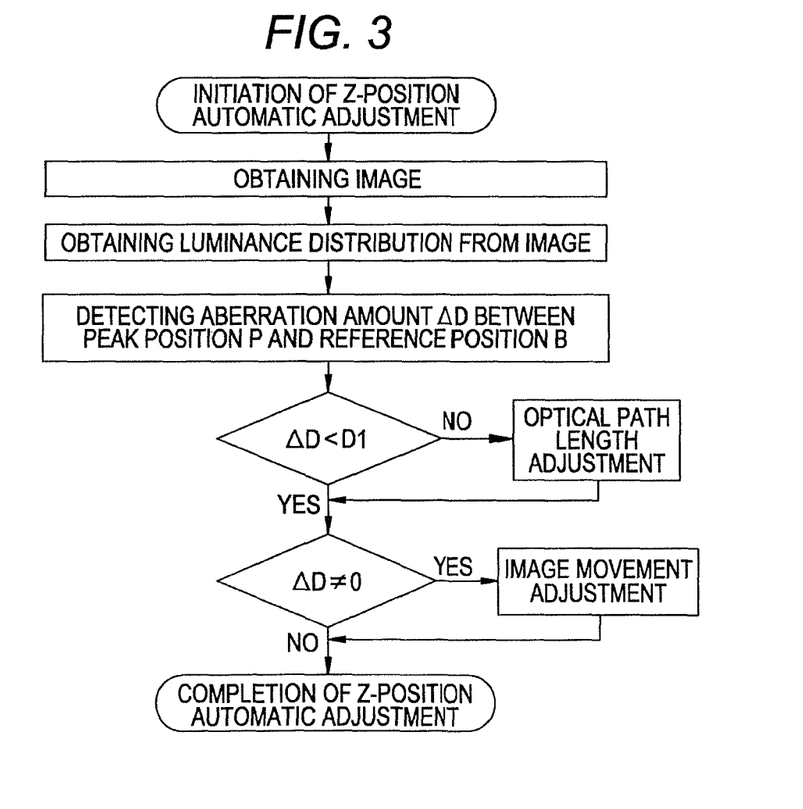
FIG. 3 is a flow chart explaining a technique for correcting a display position of the fundus tomographic image.
Figure 4A:
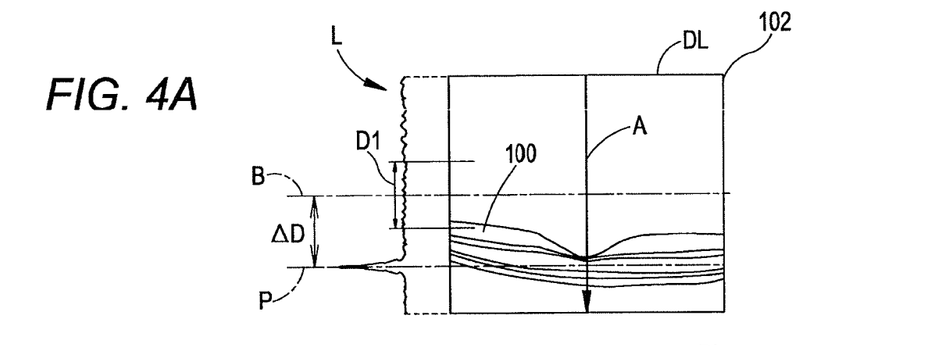
FIGS. 4A and 4B are schematic diagrams virtually illustrating a positional relationship between tomographic image data and a display region.
Figure 4B:
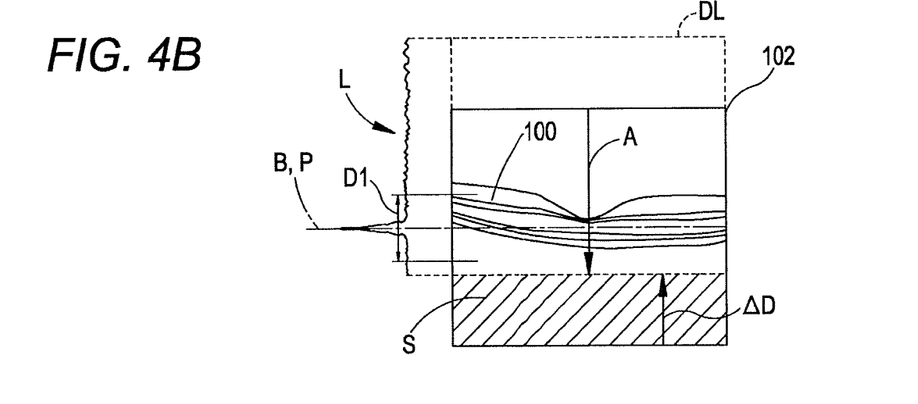

The control part 70 detects the amount of positional deviation (positional deviation information) in the depth direction of the tomographic image based on an output signal from the light receiving element 68 (refer to FIGS. 3, 4A, and 4B). The amount of the detected positional deviation may also be detected, for example, based on the obtained tomographic image, and it may also be detected based on an A scan signal at an arbitrary scanning position before image formation.

Figure 5:
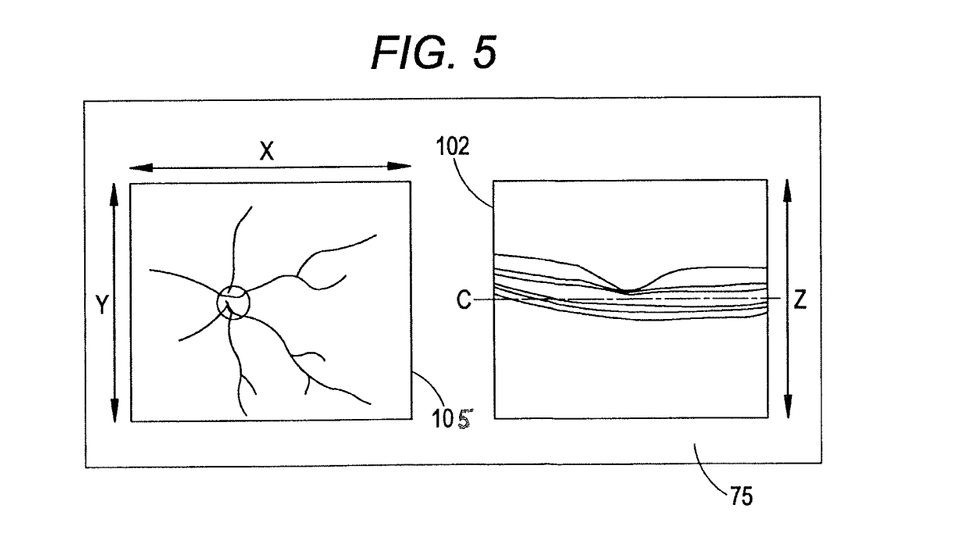
FIG. 5 is a view showing monitors on which a fundus front image and a fundus tomographic image which has been image processed are displayed.

The control part 70 corrects the display position of the tomographic image by controlling the display of the monitor 75 based on the detected amount of positional deviation. Thereby, the tomographic image which is obtained at any time is displayed at a predetermined position (for example, a center position C in the depth direction) within the display region of the monitor 75 (refer to FIGS. 3 and 5). The predetermined position described above is not limited to the center position, and may be set to any arbitrary position (for example, the upper part of the display region 102). However, the predetermined position must be a position at which the tomographic image can be sufficiently displayed. Further, the predetermined position described above may also be changed based on an operating signal from the operating part 74 operated by the examiner.

When correcting the display position, if the amount of the detected positional deviation which is detected is larger than a predetermined allowable range, the control part 70 may adjust the position of the reference mirror 31 so that the amount of the detected positional deviation which is detected falls within the predetermined allowable range by controlling the driving of the driving mechanism 50 (refer to FIG. 3).

As will be explained below, after correcting the display position of the tomographic image by moving the reference mirror 31, the control part 70 corrects the display position of the tomographic image by controlling the display of the monitor 75 using image processing.

Figure 2:
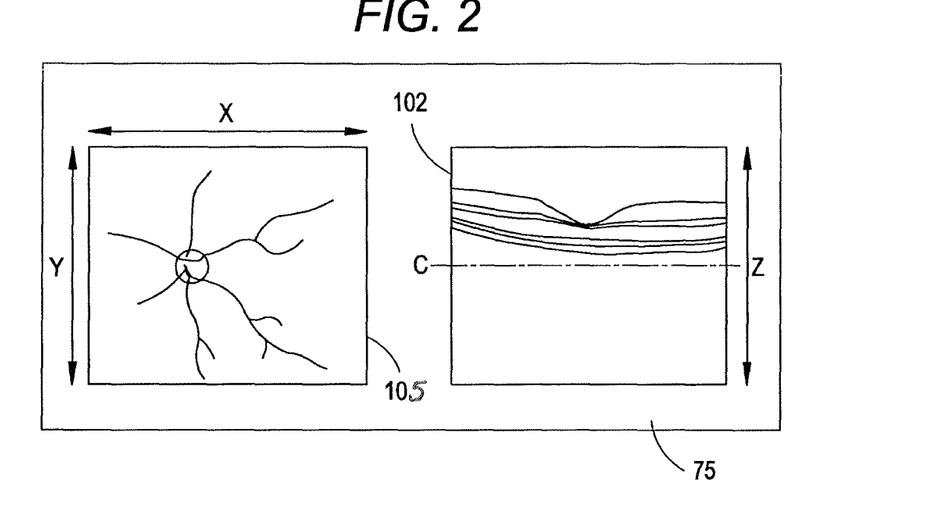
FIG. 2 is a view showing monitors on which a fundus front image and a fundus tomographic image are displayed.

Next, a detailed example of the operation of the apparatus will be explained. The examiner directs an examinee to gaze at a fixation light (not illustrated), and then performs alignment on the fundus. Next, as shown in FIG. 2, when an SLO fundus image is displayed in an SLO image display region 105 on the monitor 75, an OCT image is obtained by an OCT optical system 200 based on a predetermined scanning pattern. Thereby, the OCT image is displayed in an OCT image display region 102 on the monitor 75.

In this case, the control part 70 controls driving of the driving mechanism 50 based on a light receiving signal output from the light receiving device 83, to adjust the optical path difference between the measurement light and the reference light such that the fundus tomographic image is obtained. Next, the reference mirror 31 is moved inside a predetermined movement range corresponding to the difference in ocular axial length of the examinee's eye.

The control part 70 moves the reference mirror 31 in a predetermined step corresponding to a photographic range in the depth direction (for example, 2 mm). The control part 70 then sets scanning lines extending in the depth direction on the images obtained at each position. Next, the control part 70 obtains the luminance distribution of the images on the scanning lines. When the luminance distribution corresponding to the fundus tomographic image (for example, a luminance distribution having an abrupt rise in luminance) has been obtained, the fundus tomographic image is displayed in the display region 102 on the monitor 75.

Next, the control part 70 continuously corrects the display position of the image by image processing and adjusting the position of the reference mirror. Thereby, a fundus tomographic image obtained at a predetermined frame rate is constantly displayed in the center position C of the display region 102.

<Image Processing>

The control part 70 detects the positional deviation of the tomographic image in the depth direction based on the obtained tomographic image. Subsequently, the control part 70 controls the display of the monitor 75 based on the detection result to display a predetermined area of the fundus tomographic image (for example, the retinal pigment epithelium) on the monitor 75 at a predetermined position (for example, the center position C).

<Movement of the Reference Mirror>

If the detected positional deviation is large, the control part 70 controls the driving of the driving mechanism 50 based on the positional deviation detection result which is detected to move the reference mirror 31. Thereby, the control part 70 adjusts the positional deviation to fall within the predetermined allowable range.

FIG. 3 is a flow chart for explaining the example of display position correction of the fundus tomographic image. First, as shown in FIGS. 4A and 4B, the control part 70 sets scanning lines extending in the depth direction (an A scanning direction) on the fundus tomographic image. The control part 70 then obtains the luminance distribution L on these scanning lines. Next, the position in the depth direction at which the luminance value is maximum (hereinafter, abbreviated to "maximum luminance value") is detected from the luminance distribution L, and this position is set as a peak position P. A reference position B is the center position in the depth direction of the tomographic image, and corresponds to the center position C in the display region 102 on the monitor 75.

The control part 70 then detects a deviation amount $\Delta D$ between the peak position P and the reference position B of the captured image based on the obtained luminance distribution L. At this time, the detection of the deviation amount $\Delta D$ and the optical path length adjustment is carried out in pixel units.

<Movement of the Reference Mirror>

Next, the control part 70 determines whether the detected deviation amount $\Delta D$ is in a predetermined allowable range D1, and adjusts the optical path length based on this determination result. If the detected deviation amount ΔD is larger than the allowable range D1, the control part 70 moves the reference mirror 31 in a direction in which the deviation amount will become smaller. Thereby, the display position of the fundus tomographic image in the display region 102 is corrected. If the detected deviation amount ΔD is smaller than the allowable range D1, the control part 70 does not move the reference mirror 31.

<Image Processing>

At the same time as the optical path length adjustment, if the detected deviation amount ΔD is 1 pixel or larger (if a deviation is detected), the control part 70 also displays the captured fundus tomographic image on the monitor 75 in a state in which it has been moved by image processing.

FIGS. 4A and 4B virtually illustrate the positional relationship between the obtained tomographic image data and the display region 102. FIG. 4A illustrates the positional relationship before image processing, and FIG. 4B illustrates the positional relationship after image processing.

In this image processing, the control part 70 moves the captured image (DL) in the direction of the reference position B by the detected deviation amount ΔD (refer to FIG. 4B) to match the reference position B and the peak position P to each other. The control part 70 then displays the captured image after image processing in the display region 102 (refer to FIG. 5). In this way, even if the obtained position (peak position) of the fundus tomographic image is obtained in a state in which it is displaced from the reference position B, the display position of the fundus tomographic image is corrected so that the predetermined area of the fundus tomographic image is displayed at the center position C of the display region 102 on the monitor 75.

At this time, a space S generated by the movement of the image is displayed upon attunement to the overall background color of the display image. Further, if the deviation amount is small or there is no deviation amount, the correction of the image position is not performed. In this case, the obtained fundus tomographic image is introduced into the memory 72 and then displayed on the monitor 75 as a moving image.

As explained above, the control part 70 sequentially introduces the tomographic images into the memory 72. The control part 70 performs display position correction for each single frame in a time-series to display an image after position correction on the monitor 75. After the first image position correction, if there is a change in the image position, image position correction is carried out continuously for each frame in the same way as the above-described correction method to display a moving image on the monitor 75.

In the embodiment, for example, 50 pixels are set as the allowable range D1. This corresponds to 1/10 of an image data set to 512×512 pixels. Further, a maximum movement distance of the reference mirror 31 while obtaining a fundus tomographic image of one frame may be set to D2 (for example, approximately 10 pixels). Thus, if the deviation amount from the limit position of the allowable range D1 is D2 or greater, the control part 70 gradually moves the position of the tomographic image over several frames while moving it by D2 in each single frame. If the deviation amount from the limit position of the allowable range D1 is smaller than D2, then the control part 70 moves the position of the tomographic image by the detected deviation amount ΔD in each single frame.

In a state in which the fundus tomographic image is being movie-displayed, a desired scanning position/pattern is set by the examiner, and a predetermined trigger signal is output. Accordingly, the control part 70 obtains a tomographic image based on the set scanning position/pattern, and stores the obtained image data in the memory 72. Further, at this time, the control part 70 stores a fundus front image obtained by the SLO optical system 300 in the memory 72.

As described above, in the fundus photographing apparatus in accordance with the embodiment, the control part 70 corrects the display position of the tomographic image by image processing in each frame. Thereby, shaking of the tomographic image resulted from breathing or a slight quiver of the body can be suppressed. Therefore, a tomographic moving image can be stably displayed at a predetermined display position. Further, blurring of the tomographic image resulted from vibrations of a motor can also be avoided. Thus, even if the examinee's eye moves, the fundus tomographic image on the monitor 75 will appear with no shaking and no movement from the predetermined position.

Moreover, if the amount of the detected positional deviation is larger than a predetermined allowable range, the control part 70 moves the reference mirror so that the amount of the detected positional deviation falls within the predetermined allowable range. Thereby, a large positional deviation of the fundus of the examinee's eye can be handled. For example, even in the case that a tomographic image is obtained while changing the observation position by changing the fixation position, or even in the case that the examinee's forehead moves relative to a forehead pad (not illustrated), the tomographic image will not deviate from the display screen. Therefore, the trouble required for readjusting the optical path length can be avoided. Further, even in the case that the examinee's eye moves by an amount that falls in the predetermined display region, the tomographic image can be displayed at a nearly constant sensitivity by moving the reference mirror.

Regarding the optical path length adjustment described above, the setting of the allowable range D1 will be explained below. Complication may arise because the reference mirror 31 must be constantly moved in order to completely eliminate the deviation amount by adjusting the optical path length. Therefore, by setting the predetermined allowable range D1, continuous movement of the reference mirror is prevented.

The predetermined allowable range D1 is preferably larger than a comparatively small amount of positional deviation corresponding to micromotion of the tomographic image resulted from fluctuations in the interference light, noise, breathing of the examinee, and the like, and smaller than a positional deviation exceeding the comparatively small amount of positional deviation (for example, a positional deviation generated when the forehead moves relative to the forehead pad). Thereby, in the case that the tomographic image moves slightly, the reference mirror 31 is not moved, whereas when an amount of positional deviation exceeding micromotion is detected, the reference mirror 31 is moved.

The predetermined allowable range D1 may also be a range which is larger than a comparatively small amount of positional deviation at which the entire tomographic image can be sufficiently observed even if the tomographic image deviates from the predetermined position, and smaller than a positional deviation exceeding the comparatively small amount of positional deviation.

The predetermined allowable range D1 may also be a range corresponding to a large amount of positional deviation at which the fundus tomographic image deviates from the display region 102. In this case, the reference mirror 31 is moved only when this kind of large amount of positional deviation is detected.

If the detected amount of positional deviation is larger than the predetermined allowable range, the control part 70 may also simultaneously correct the display position of the tomographic image by controlling the display of the monitor 75 and adjust the position of the reference mirror 31 by controlling the driving of the driving mechanism 50.

In addition, the control part 70 may also adjust the position of the tomographic image by only controlling the display of the monitor 75 using image processing without moving the reference mirror 31, without consideration to the amount of the detected positional deviation of the tomographic image.

In the above explanation, the adjustment of the optical path length was carried out automatically until a fundus tomographic image is first obtained. However, the embodiment is not limited to this configuration, and the optical path length may be adjusted based on an operation by the examiner viewing the monitor 75. In the case that the detected deviation amount ΔD deviates from the predetermined allowable range D1, the optical path length may be adjusted based on an operation by the examiner viewing the monitor 75.

In the above explanation, when correcting the position of the tomographic image by image processing, the tomographic image is moved to a predetermined display region. However, the embodiment is not limited to this configuration, and, for example, an extracted region of an image which is output to the predetermined display region in the image data of the tomographic image may also be changed.

In the embodiment, in order to detect the positional deviation of the tomographic image, a method is used in which the deviation between the peak value and the reference position in accordance with the luminance distribution is detected to detect the positional deviation. However, the embodiment is not limited to this configuration, and in order to detect the positional deviation, for example, various image processing methods can be used (a method using various correlation functions, a method utilizing Fourier transform, a method based on matching of characteristic points). In such a case, for example, a tomographic image in which there is no positional deviation is set as a reference image, and the amount of the detected positional deviation relative to the reference image is calculated.

In the above explanation, in order to adjust the optical path difference between the measurement light and the reference light, an optical-path-length varying member is provided in the optical path of the reference light. However, the embodiment is not limited to this configuration, and the optical-path-length varying member may also be provided in the optical path of the measurement light. In this case, for example, the collimator lens 22 and the end of the optical fiber 39b are moved in the optical axis direction.

In the embodiment, an aspect of the invention is applied to a fundus photographing apparatus, which is one example of an ophthalmic photographing apparatus. However, the embodiment is not limited to this configuration, and it is also possible to apply the aspect of the invention to an ophthalmic photographing apparatus for photographing a tomographic image of a predetermined area of an examinee's eye (for example, an anterior segment tomographic image) using an optical interference optical system formed by applying the OCT principle.

The aspect of the invention is not applied only to ophthalmic photographing apparatuses. The aspect of the invention is also applicable to an optical tomographic image photographing apparatus for photographing a tomographic image of an organism other than the eye (for example, skin and veins), an object other than an organism, or the like.

The ophthalmic photographing apparatus in accordance with the embodiment may also have a configuration for tracking a measurement light scanned on an object relative to the object. As such a configuration, for example, a frontal optical system that obtains a front image of an object can be used. In the case that such a frontal optical system is used, the control part 70 detects a deviation of the scanning position on the object with respect to the XY directions at any time based on the front image obtained by the frontal optical system. The control part 70 then corrects the deviation in the scanning position by controlling an optical scanner (for example, the scanning part 23) to correct the scanning position of the measurement light.

In order to detect deviations of the scanning position, the control part 70, for example, detects by image processing a positional deviation between front images obtained at any time. As a method for detecting positional deviation of the front images, various image processing methods can be used (a method using various correlation functions, a method utilizing Fourier transform, a method based on matching of characteristic points). In such a case, for example, a tomographic image in which there is no positional deviation is set as a reference image, and the amount of the detected positional deviation relative to the reference image is calculated.

As an optical system for obtaining a front image of an object, for example, an SLO optical system or a CCD camera can be used. Further, a front image is obtained by an interference optical system (for example, the OCT optical system 200). The control part 70 scans the measurement light in two dimensions using an optical scanner (for example, the scanning part 23). The control part 70 then obtains a front image based on a light receiving signal output from a detector (for example, the light receiving element 83). For example, an integrated value of spectral data at each position in the X direction and the Y direction is used as the luminance value of the image.

In the embodiment, the control part 70 moves the optical-path-length varying member (the reference mirror 31) by controlling the driving of the driving mechanism 50, and thereby mechanically corrects the display position of the tomographic image. However, the control part may also control the driving of a driving part for mechanically correcting the display position of the tomographic image which is not limited to the driving mechanism 50.

As such a driving part, for example, a moving unit 6 for moving the entire interference optical system 200 relative to the object is cited. In the case of controlling the driving of the moving unit 6, if the detected positional deviation is larger than the predetermined allowable range, the control part 70 adjusts the position of the entire interference optical system by controlling the moving unit 6. In the case that the object is an eye, the control part 70 may also control the driving of an observation optical system 90 as a configuration for detecting movement of the eye. Further, in this case, the control part may also control the driving of both the moving unit 6 and the driving mechanism 50 as a mechanical driving part.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An optical tomographic image photographing apparatus for photographing a tomographic image of an object, comprising:
   an interference optical system including:
      a measurement light source; and
      a splitter configured to split light emitted from the measurement light source, such that the light is split into a measurement optical path for guiding a part of the light to the object as measurement light and into a reference optical path for generating reference light, the interference optical system configured to combine reflected light from the measurement optical path, the reflected light being obtained by reflection of the measurement light on the object, with the reference light from the reference optical path, to guide combined light to a detector;

an optical scanner arranged in the measurement optical path for scanning the measurement light on the object;

a driving part configured to move an optical member arranged in the measurement optical path or the reference optical path in an optical-axis direction in order to adjust an optical path difference between the measurement optical path and the reference optical path;

an image obtaining part connected to the detector for obtaining a tomographic image of the object based on a light receiving signal output from the detector;

a monitor; and a control unit configured to detect positional deviation of the tomographic image in a depth direction thereof based on the signal output from the detector, and perform image processing, based on the detected positional deviation, to correct a display position of the tomographic image such that the tomographic image obtained by the image obtaining part is displayed in a predetermined position on the monitor.

2. The optical tomographic image photographing apparatus according to claim 1, wherein the control unit is configured to adjust a position of the optical member in the optical axis direction by controlling the driving part, in a case that the detected positional deviation is larger than a predetermined allowable range.

3. The optical tomographic image photographing apparatus according to claim 2, wherein the control unit is configured to adjust the position of the optical member such that the detected positional deviation falls within the predetermined allowable range.

4. The optical tomographic image photographing apparatus according to claim 2, wherein the control unit is configured to simultaneously perform (i) the image processing to correct the display position of the tomographic image on the monitor and (ii) adjustment of the position of the optical member by controlling the driving part, in the case that the detected positional deviation is larger than the predetermined allowable range.

5. The optical tomographic image photographing apparatus according to claim 2, wherein the control unit is configured to adjust the position of the optical member when the detected positional deviation exceeds predetermined positional deviation corresponding to micromotion of the tomographic image.

6. The optical tomographic image photographing apparatus according to claim 2, wherein the control unit is configured to adjust the position of the optical member when the detected positional deviation exceeds predetermined positional deviation at which an entire tomographic image sufficiently observable.

7. The optical tomographic image photographing apparatus according to claim 1, wherein the object is an eye.

8. The optical tomographic image photographing apparatus according to claim 7, wherein the tomographic image is an Optical Coherence Tomography (OCT) image of the fundus of the eye.

9. The optical tomographic image photographing apparatus according to claim 8, wherein the control unit is configured to detect the positional deviation of the tomographic image in a depth direction of the eye.

10. The optical tomographic image photographing apparatus according to claim 1, further comprising:

an optical system configured to obtain a front image of the object; and a scanning position correction unit configured to detect deviation of a scanning position of the measurement light on the object in a horizontal direction and a vertical direction based on the obtained front image, and correct, by controlling the optical scanner, the scanning position of the measurement light such that the deviation of the scanning position is corrected.

11. The optical tomographic image photographing apparatus according to claim 1, wherein the control unit is configured to continuously correct the display position of the tomographic image.

12. The optical tomographic image photographing apparatus according to claim 1, further comprising:

a moving unit configured to move the entire interference optical system relative to the object, wherein the control unit is configured to adjust a position of the entire interference optical system by controlling the moving unit, in the case that the detected positional deviation is larger than a predetermined allowable range.

13. The optical tomographic image photographing apparatus according to claim 1, further comprising:

a driving part configured to mechanically correct the display position of the tomographic image under control of the control unit.

14. The optical tomographic image photographing apparatus according to claim 1, wherein the control unit is configured to detect the positional deviation of the tomographic image as a deviation amount between a reference position and a peak position having a maximum luminance value in the tomographic image.

15. The optical tomographic image photographing apparatus according to claim 14, wherein the control unit is configured to perform the image processing to match the reference position and the peak position to each other.

16. The optical tomographic image photographing apparatus according to claim 1, wherein the control unit is configured to detect the positional deviation of the tomographic image relative to a reference tomographic image.

* * * * *